United States Patent [19]
Berthaud et al.

[11] Patent Number: 5,128,621
[45] Date of Patent: Jul. 7, 1992

[54] DEVICE FOR MEASURING, AT A PLURALITY OF POINTS, THE MICROWAVE FIELD DIFFRACTED BY AN OBJECT

[75] Inventors: Patrice Berthaud, Suresnes; Jean-Charles Bolomey, Paris, both of France

[73] Assignee: Centre National de la Recherche Scientifique, France

[21] Appl. No.: 427,116

[22] PCT Filed: Apr. 20, 1988

[86] PCT No.: PCT/FR88/00191
§ 371 Date: Dec. 3, 1990
§ 102(e) Date: Dec. 3, 1990

[87] PCT Pub. No.: WO88/08529
PCT Pub. Date: Nov. 3, 1988

[30] Foreign Application Priority Data
Apr. 21, 1987 [FR] France ................................ 87 05597

[51] Int. Cl.⁵ .................. G01N 22/00; K01Q 19/06
[52] U.S. Cl. ..................................... 324/639; 324/636; 343/754
[58] Field of Search ............... 324/639, 637, 640, 641, 324/632; 343/754, 700 MS, 771

[56] References Cited

U.S. PATENT DOCUMENTS

| | | | |
|---|---|---|---|
| 3,708,796 | 1/1973 | Gilbert | 343/754 |
| 4,212,014 | 7/1980 | Chekroun | 343/754 |
| 4,271,389 | 6/1981 | Jacobi et al. | 324/639 |
| 4,297,708 | 10/1981 | Vidal | 343/754 |
| 4,531,126 | 7/1985 | Sadones | 343/754 X |
| 4,546,311 | 10/1985 | Knöchel | 324/640 |
| 4,552,151 | 11/1985 | Bolomey et al. | 343/754 X |
| 4,634,968 | 1/1987 | Aslan . | |

FOREIGN PATENT DOCUMENTS

| | | |
|---|---|---|
| 0065455 | 11/1982 | European Pat. Off. . |
| 0069628 | 1/1983 | European Pat. Off. . |
| 0217111 | 4/1987 | European Pat. Off. . |

*Primary Examiner*—Jack B. Harvey
*Attorney, Agent, or Firm*—Rosenman & Colin

[57] ABSTRACT

An arrangement for measuring, at a plurality of points, the microwave field diffracted by an object. A microwave radiation source illuminates an object. Electric doublet antennae loaded by diodes are disposed in line along the path of the radiation diffracted by the object. A guide structure, with coupling antennae, is disposed along the line of doublet antennae and collects the diffracted radiation. Electronic circuits control the whole so as to measure the diffracted field at the position of each doublet antenna.

21 Claims, 5 Drawing Sheets

DEVICE FOR MEASURING, AT A PLURALITY OF POINTS, THE MICROWAVE FIELD DIFFRACTED BY AN OBJECT

BACKGROUND OF THE INVENTION

1. Field of the Invention

The present invention relates to a device for measuring, at a plurality of points, the microwave field diffracted by an object illuminated by a microwave radiation source at a frequency and comprising:

at each of said points an electric doublet type antenna loaded at its center by a diode, means for collecting the diffracted microwave radiation and delivering a collected microwave signal, means for generating a low frequency signal, multiplexing means, disposed between said generating means and each of said diodes, and means for controlling said multiplexing means so that at least one of said diodes is biassed by said low frequency signal and, in response to said low frequency signal and said collected microwave signal, for generating a signal representative of the microwave field at the point where said doublet antenna loaded by said biassed diode is located.

Such a device may be used for numerous industrial applications and in particular for the non destructive control of objects likely to present certain defects, or else materials or products having undergone transformations such as drying, de-freezing or polymerization, for example, so as to check the results of such transformation.

2. Description of Related Art

In fact, it is known that a body illuminated by a microwave radiation source diffracts this radiation in a way which obviously depends on its shape, but also on the dielectric constant and on the conductivity at every point of its volume. Since these last two quantities depend obviously on the internal structure of the body, it is therefore possible to carry out non destructive control of the internal structure of a body by analyzing the diffraction of a microwave field illuminating this body.

By diffracted field is here meant either the field transmitted through the body or the field reflected thereby, so that the analysis of the diffraction may take place either during transmission, or reflection, or both at the same time.

Thus, by way of example, the defects of a wooden plank may be analyzed, the degree and homogeneity of drying of a panel or layer of plaster or of a sheet of paper checked, the development and result of the polymerization of a plastic material checked or the stage of de-freezing of foods evaluated.

A measuring device of this type is already known, described in U.S. Pat. No. 4,552,151. In this device, the doublet antennae are connected end to end so as to form the columns of a "matrix retina", i.e. the assembly of the doublet antennae form a rectangular panel. The collector means are formed by a stack of waveguides, each in the form of a horn and the assembly is controlled so that the value of the field may be measured successively at any point of the panel.

Such a two dimensional device is however fairly cumbersome for the length of each horn is of the order of size of the largest dimension of its openings, which substantially defines the maximum analysis length. This device is in addition of a relatively high cost price and it is relatively complex to use, particularly considering the necessity of using a microwave multiplexer. In addition, although it is suitable for biomedical applications, or laboratory applications, it is ill-fitted to industrial applications of the above type.

SUMMARY OF THE INVENTION

The object of the present invention is to overcome the above drawbacks by providing a compact measuring device of low cost and with high speed and simple operation, which is well suited to the industrial medium.

For this, the present invention provides a measuring device of the above type characterized by the fact that:

said doublet antennae are disposed along at least one line, said collector means comprise a single microwave guide structure, disposed along said doublet antennae line, on the side opposite said object at a distance from said doublet antennae, along said guide structure is provided a plurality of antennae for coupling to said guide structure, each coupling antenna transforming the microwave radiation which it receives into a wave guided by said guide structure, one end of said guide structure is provided with a termination and the other end with means for converting said guided waves into said collected microwave signal, said coupling antennae are disposed at positions such that they would all radiate in phase if, with said source extinguished, a single microwave signal were applied to said conversion means, said distance between the doublet antennae and the guide structure is determined so that, under these conditions, a uniform field is created on said doublet antennae line.

For the measuring device of the invention, because the doublet antennae are distributed over a line, and because the collector means only comprise a guide structure disposed along the same line, at a few wavelengths from the doublet antennae, the size and cost price are low. In addition, in the industrial applications mentioned above, the object examined is, in a large majority of cases, an object travelling in front of the measuring device. The arrangement of the doublet antennae line substantially perpendicularly to the travel direction will then make it possible to obtain in a simple way an image of the object.

With the prior art device, the size in the direction perpendicular to the analysis plane is of the order of a meter for an analysis length of the same order of size, whatever the wavelength, whereas in the device of the invention it is of the order of a few wavelengths, namely for example less than 10 cm for a working frequency of 9 GHz. Furthermore, for the same length of the device along the analysis line, the useful zone is larger.

In the device of the invention, it is remarkable that, because of the uniformity of the field which would be created by the coupling antennae on the doublet antenna line, the latter may be disposed at a spacing chosen solely as a function of the fineness of analysis desired in the application considered, without having to worry about the periodicity of the propagation on the guide structure. In other terms, the spacing of the doublet antennae and the spacing of the coupling antennae are chosen independently of each other, which confers on the measuring device of the invention a great flexibility in use.

In addition, the device of the invention makes it possible to measure variations of the amplitude and phase of the microwave field along the doublet antennae line, with a view to a direct display or synthetic processing or focussing at points inside the object. In the latter two cases, it is thus possible to obtain a tomographic representation of the object.

Thus, the device of the invention which is very well suited for the non destructive control of objects or materials travelling past with a view to controlling their production unit, is also suited for a more thorough analysis carried out in the laboratory, for permitting, for example, a better understanding of the transformation process which the object undergoes.

Advantageously, the volume situated between said guide structure and said doublet antennae is closed by two walls parallel to said line and covered with a layer of material absorbing the radiation at said microwave frequency.

Advantageously again, between said object and doublet antennae is provided a matching screen.

The preceding elements make it possible to optimize the device, at the microwave working frequency, by avoiding leaks and parasite reflections of the microwave radiation and permitting the matching and tuning of the doublet antennae array.

BRIEF DESCRIPTION OF THE DRAWINGS

The present invention will be better understood from the following description of several embodiments of the measuring device of the invention, with reference to the accompanying drawings in which.

DETAILED DESCRIPTION OF THE PREFERRED EMBODIMENTS

Figure 1:
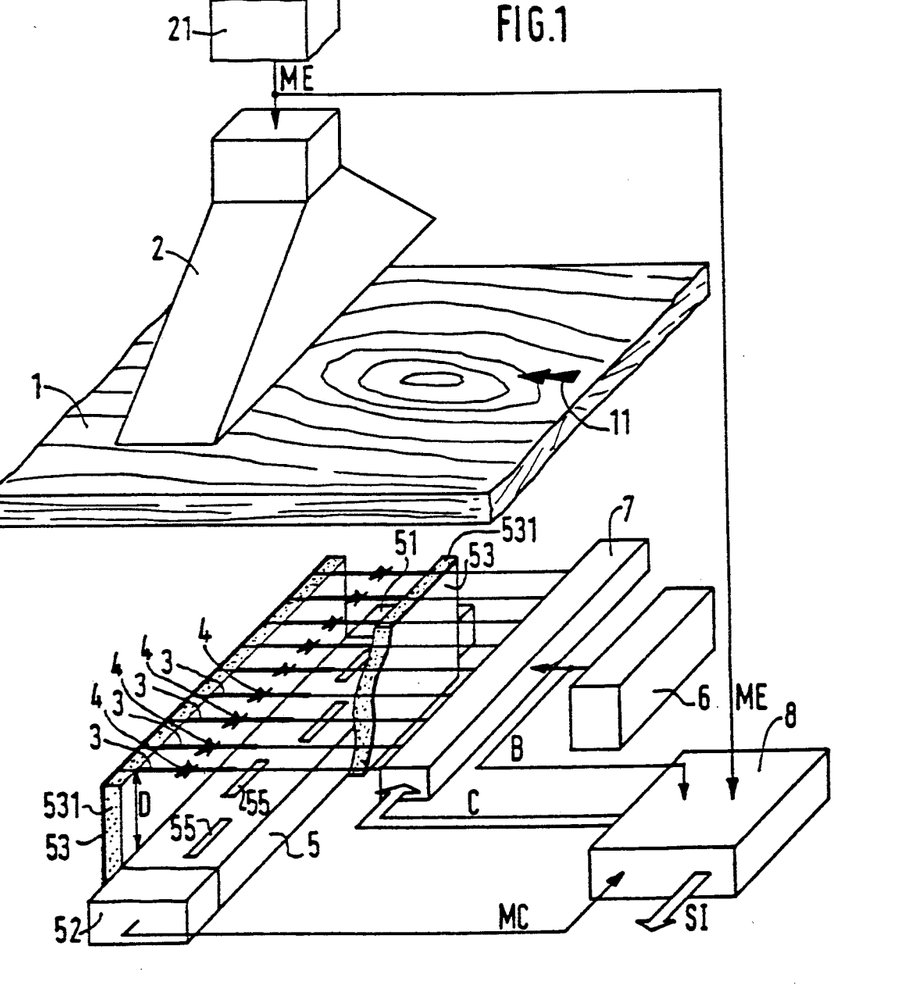
FIG. 1 is a perspective view of the device of the invention used for detecting defects in wood.

Referring to FIG. 1, a measuring system for detecting defects in a wooden plank 1 will be described. Plank 1 travels, as shown by arrow 11, in front of the fixed measuring system adapted for detecting the defects in the plank so as to control its subsequent cutting in an optimum way, for example.

A microwave radiation source, in this case a horn 2, is fed with a microwave signal ME delivered by a microwave generator 21. The microwave signal ME is a signal at a single frequency.

Horn 2 illuminates plank 1 over the whole of it width. A device for measuring the microwave field diffracted by the plank 1, which diffracted field is here the field transmitted through this plank 1, is therefore disposed opposite horn 2, on the other side of plank 1, at a distance magnified in the figure for obvious reasons of clarity.

This measuring device comprises first of all a plurality of antennae 3, of electric doublet type, i.e. each comprising two equal and aligned rectilinear sections. The cathode of a diode 4 is connected to one of the sections whereas its anode is connected to the other section, so that each of the doublet antennae 3 is loaded at its center by diode 4, here of PIN type. The doublet antennae 3 are disposed along a line, here perpendicular to the travel direction 11 of the plank, and corresponding to the elongate zone illuminated by the horn 2.

A guide structure, here a rectangular guide 5, is disposed along the line of doublet antennae 3, on the side opposite plank 1 and at a distance D equal, as will be seen further on, to a few wavelengths, at said microwave frequency and in the medium in which the operation takes place, here air.

Slots 55, whose geometrical characteristics will be described in greater detail hereafter, are formed in the large side of guide 5 which is situated opposite the line of doublet antennae 3.

At one end of guide 5 is mounted a termination 51, here a short circuit, whereas at the other end is mounted a transition 52, of the known coaxial guide type.

Two walls 53, rigid and covered with a layer 531 of material absorbing the microwave radiation at the working frequency, are disposed parallel to the line of doublet antennae 3, on each side of guide 5 for closing the volume situated between guide 5 and the doublet antennae 3. The absorbing material used is for example a plastic material foam charged with carbon of current type, for reducing the multiple reflections between guide 5 and the doublet antennae 3.

As shown in FIG. 1, each doublet antennae 3 has a section connected to the electric ground of the system, here for example by welding to one of the walls 53, which is for this purpose made from metal and grounded. The other section of each doublet antennae 3 is here connected to each of the outputs of a multiplexer 7 which receives at its single input a low frequency signal B from a generator 6.

By "low frequency signal" is here meant a periodic square of sinusoidal signal whose frequency range is considerably lower than the range of frequencies usually called microwave. Thus, since we can say that the microwave range is limited downwards to a few hundred MHz, the signal B will in general have a frequency less than a few tens of MHz.

An electronic circuit 8, controlled by a microprocessor, is provided with two microwave inputs receiving the microwave signal ME and a microwave signal MC delivered by the transition 52, a low frequency input receiving the signal B, a digital output delivering a signal C for controlling the multiplexer and an output delivering a signal SI, representative of the microwave field measured and applied for example to a display device, not shown because it is known.

The device which has just been described operates as follows.

At all times, the microprocessor of the electronic circuit 8 controls the multiplexer 7 so that signal B is applied to a single one of the diodes 4. Thus, only this diode is biassed, successively reversely and forwardly, at the timing of signal B.

Simultaneously, the microwave radiation illuminates plank 1 and the field diffracted at the level of each of the doublet antennae 3 is a sample of a microwave image of the slice of plank illuminated.

Each slot 55 acts moreover as a coupling antenna to guide 5, for transforming the radiation which it receives, and in particular the radiation from the array of doublet antennae 3, into a wave guided by guide 5.

The guided waves from the different slots 55 are converted into the microwave signal MC by the transition 52. The microwave signal MC is called collected microwave signal since it results from the collection of the radiation received by the different slots 55 and in particular the radiation from the array of doublet antennae 3.

In the electronic circuit 8 the collected microwave signal undergoes synchronous microwave detection by means of the microwave signal ME, then a second low frequency synchronous detection by means of signal B. Now, among all the collected radiation, only the radiation from the doublet antennae 3, loaded by the diode biassed by signal B, is modulated by this signal B. Thus, the signal MC, after microwave then low frequency detection is only representative of the field at the point where the doublet antenna 3 is located, loaded by diode 4 which is biassed by means of signal B. The microprocessor of circuit 8 may therefore control the successive biassing of each of diodes 4 and elaborate, from the signal C which indicates the position of the measuring point, and from the signal resulting from the double detection which indicates the value of the field at this measuring point, a signal SI for controlling the display device.

This type of operation, which results from the use of the method known to a man skilled in the art under the name "modulated diffusion method" is described in the already mentioned U.S. Pat. No. 4,552,151.

This type of operation is not the only one which may be considered for the device of the invention. Thus, by providing on each of the outputs of multiplexer 7, a controllable low frequency phase shifter, by controlling the multiplexer so that the diodes are biassed simultaneously, in accordance with the teaching of French patent 86 05 205, the device can be focussed on an inner point of a thick plank, thus making possible a tomographic type representation.

The electronic circuit 8, which therefore comprises mainly a control microprocessor and a synchronous microwave detector followed by a synchronous low frequency detector, is within the scope of a man skilled in the art and will not be further described.

Figure 2:
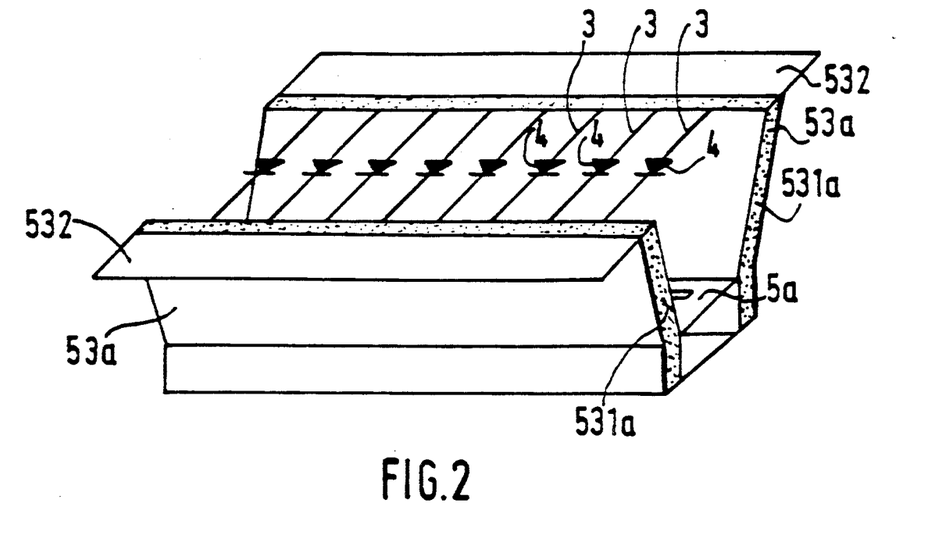
FIG. 2 shows a variant of construction of the guide structure and of the side walls of the measuring device of FIG. 1.

FIG. 2 shows a variant of construction of the side walls of the device of the invention. In this Figure, guide $5a$ is narrower than guide 5 and the side walls $531a$ widen out and they end in two metal flanges 532 extending in the plane of the doublet antennae 3.

Figure 3:
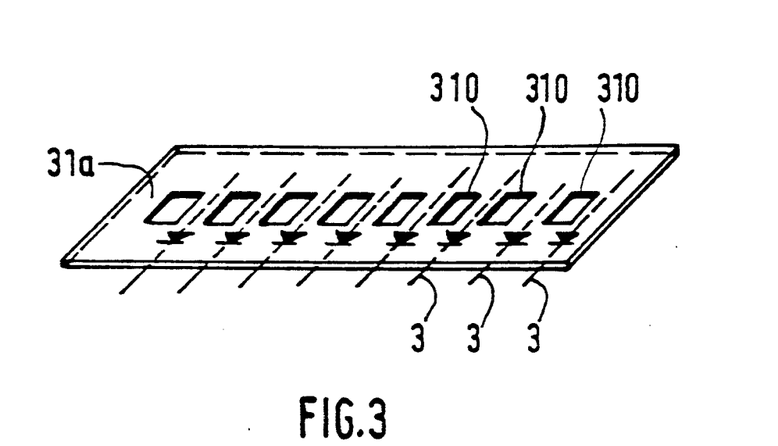
FIG. 3 shows a matching screen for the doublet antennae of the measuring device of FIG. 1.
Figure 4:
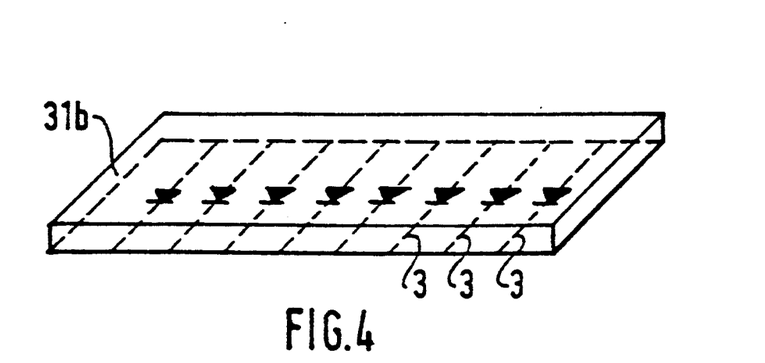
FIG. 4 is a variant of construction of the matching screen of FIG. 3.

In FIGS. 3 and 4 are shown two variants of construction of a matching screen which may be disposed between plank 1 and the doublet antennae 3.

In FIG. 3, a metal plate $31a$ is provided with openings 310 disposed opposite each doublet antennae 3. The size of the openings and their distance to the doublet antennae are determined and adjusted experimentally, taking into account the application considered so as to obtain good matching of the antennae, i.e. to make the microwave power reflected by the doublet antennae towards the object examined minimum.

In FIG. 4, a single thick dielectric plate $31b$ is used as matching screen. Here again, the dielectric constant of the plate, as well as its thickness, are determined and adjusted experimentally so as to obtain good matching.

Figure 5:
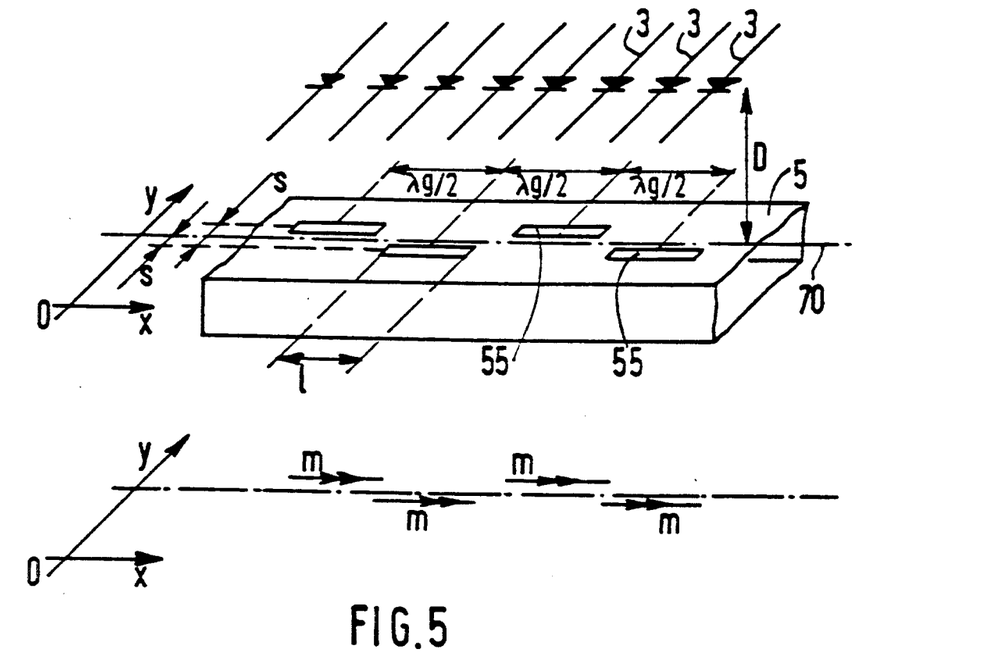
FIGS. 5, 6, 7, 8 and 9 each show a variant of the guide structure and of the doublet antennae of the measuring device of FIG. 1.

FIG. 5 shows in greater detail the arrangement of slots 55 in guide 5 of FIG. 1. Slots 55 are here formed in the large side of guide 5 and the doublet antennae 3 are all perpendicular to the line along which they are disposed. Slots 55 are longitudinal, of length l and are disposed alternately on each side of the median axis 70 of the large side of the guide, at a distance s from this axis 70. Two successive slots are separated by a guided wave half-length, namely $\lambda g/2$ at the working frequency. They have a length close to the radiated wavelength, namely $\lambda/2$, at the working frequency, and small width, but whose value is not critical.

The operation of the coupling antennae formed by means of slots 55 is easy to understand and to characterize if we assume that horn 2 is not radiating and if we assume that a microwave signal is applied to the transition 52. Although the use for which the device of the invention is provided does not correspond to this operating assumption, we come to it by the theorem of reciprocity, well known to a man skilled in the art. Such an assumption facilitates understanding of the operation of the slots.

If therefore we assume that a microwave signal is applied to transition 52, the guided wave in guide 5 is in phase opposition opposite each of the successive slots 55, since they are spaced apart by $\lambda g/2$. However, because of their alternation with respect to the median axis 70, slots 55 all radiate in phase. In addition, they are fairly close together so as to create a uniform field along the doublet antennae line 3, disposed at the distance D of a few radiated wavelengths. In this case, and as already mentioned, the doublet antennae 3 may be spaced apart by a distance which is the best suited to the analysis of the object, independently of the periodicity of propagation in guide 5. Here, and depending on the desired fineness of analysis, the spacing between the doublet antennae 3 is between a few millimeters and a few centimeters.

The distance s may be determined for example in the following way. If guide 5 includes in all N slots having a reduced conductance equal to g, good matching requires:

$g = 1/N$ and reference is then made to charts for determining, as a function of the reduced conductance g, the value of distance s. Such charts are well known to a man skilled in the art and are available in particular in the following work: "Antenna Engineering Handbook", Ed, Henry JASIX, Chap. 9; Slot antenna arrays, MacGraw Hill, N.Y., 1984.

As shown in the lower part of FIG. 5, slots 55 are equivalent, in the plane xOy of the large side of guide 5 to magnetic doublets m perpendicular to the electric doublet antennae 3.

Figure 6:
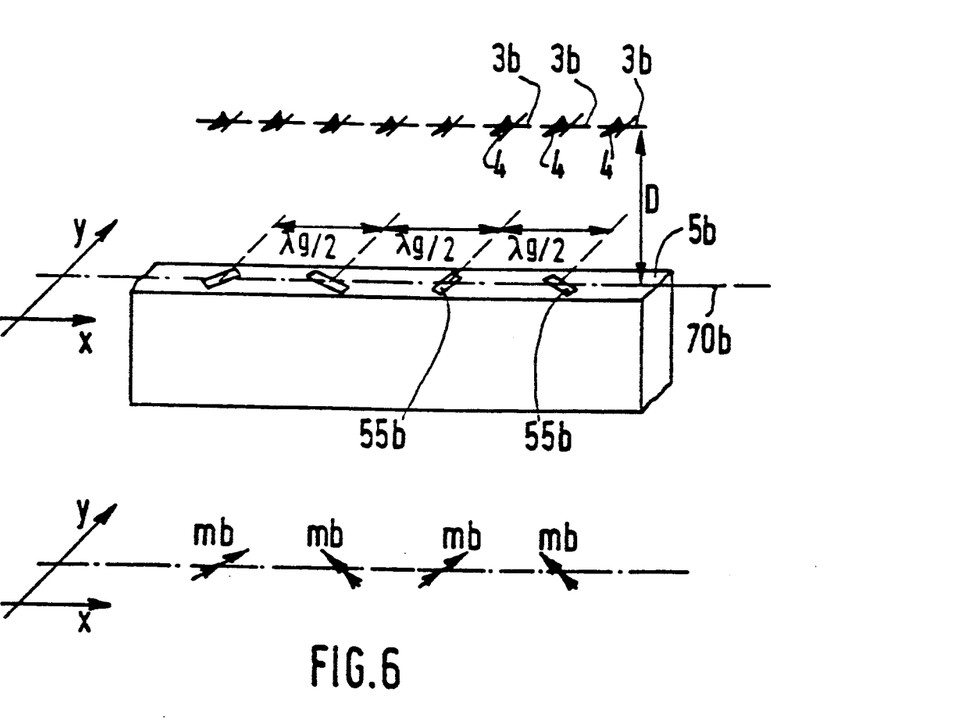

FIG. 6 shows a variant of construction in which the doublet antennae $3b$ are all parallel to the line along which they are disposed. A rectangular guide $5b$, in the small side of which are formed slots $55b$, is disposed so that these slots $55b$ are opposite the doublet antennae $3b$. Slots $55b$ are spaced apart by $\lambda g/2$ and form, with the median axis $70b$ of the small side equal and alternately opposite angles. Slots $55b$ act like coupling antennae equivalent to magnetic doublets $m_b$. They would radiate in phase if a microwave signal were applied to guide $5b$ and would then create a field whose resultant, in the direction of the doublet antennae 3b, would be uniform at the level of these doublet antennae 3b.

Figure 7:
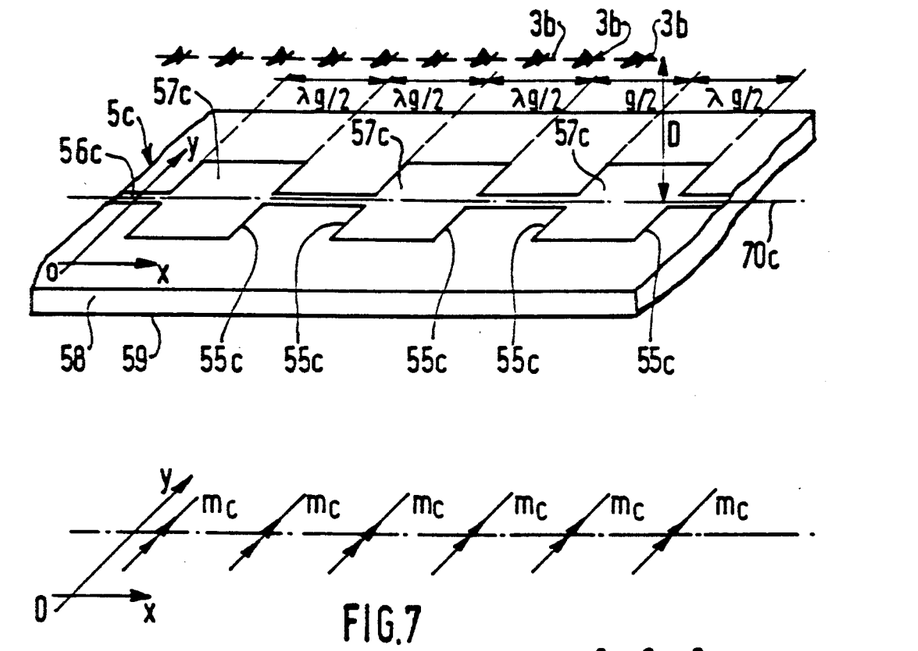

In FIG. 7 is shown another variant of the device of the invention. The doublet antennae 3b remain oriented as in the preceding example, namely parallel to their alignment but the guide structure is now a microstrip line 5c which includes, in a way known per se, a dielectric plate 58, having one face coated with a metallic layer connected to the electric ground, the other face supporting a conducting microstrip 56c. As shown in FIG. 7, microstrip 56c is widened periodically so as to form rectangular metal patches 57c connected therefore in series to the microstrip line 5c. It is known that the edges 55c, perpendicular to microstrip 56c, of rectangles 57c are equivalent, because of the deformation of the field lines, to magnetic dipoles $m_c$ which are here perpendicular to the doublet antennae 3b. Line 5c is provided so that the edges 55c are spaced apart by $\lambda g/2$, so that, as for the slots 55 of guide 5, they all radiate in phase when a microwave signal is applied to the microwave line 5c.

Figure 8:
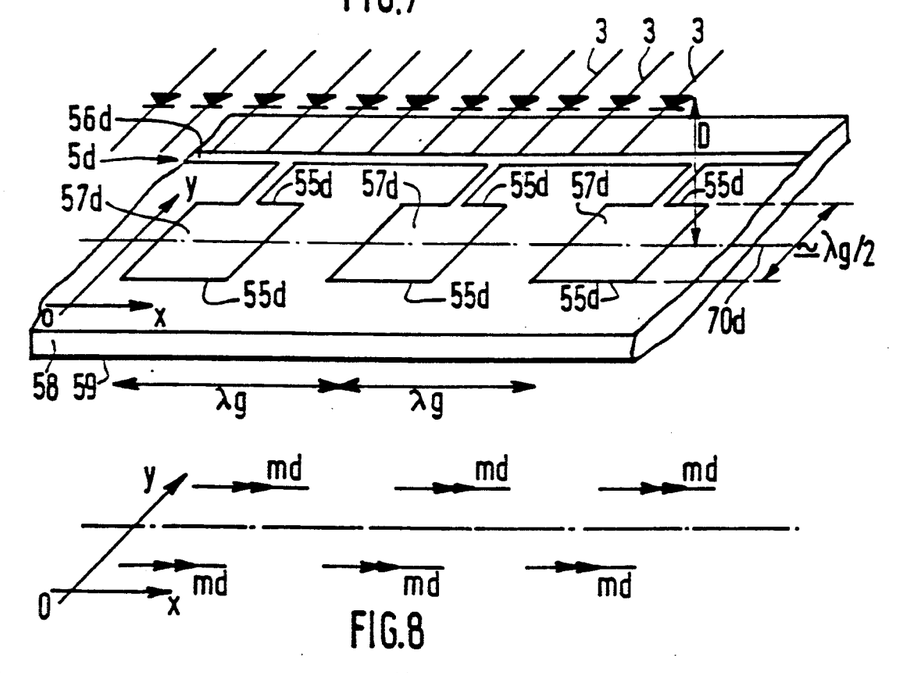

FIG. 8 shows another variant in which the guide structure is the microwave line 5d, but which is adapted so as to be suitable for the doublet antennae 3, oriented perpendicularly to their alignment. In FIG. 8, rectangular metal plates 57d are shunt connected to microstrip 56d of line 5d, but perpendicularly to this line 5d, so that the two edges 55d, parallel to line 5d, of plates 57d act like magnetic doublets $m_d$ perpendicular to the electric doublet antennae 3. Here again, line 5d is designed so that the coupling antennae 55d are fed in phase by a signal applied to line 5d. Here, the shuts are spaced apart by a guided wavelength $\lambda g$ and the edges 55d are spaced apart by $\lambda g/2$.

The operation of these patch antennae is described in the work already mentioned "Antenna Engineering Handbook", Ed Henry JASIX, Chap. 7; Microstrip antennas, MacGraw Hill, N.Y., 1984.

It should be noted that, although it is practical to place the coupling antennae so that they are spaced apart by a guided wave half length, while adjusting the symmetries of their positions so that they radiate in phase, this is not obligatory and they may be placed for example so that they are spaced apart by a guided wavelength, by disposing them at identical positions. The only criterion to be respected is that the coupling antennae must be disposed so as to all radiate in phase, at positions which are sufficiently close so that, under these conditions, a uniform field is created on the doublet antennae line 3, the distance between these doublet antennae and the guide structure remaining sufficient to avoid coupling phenomena.

Figure 9:
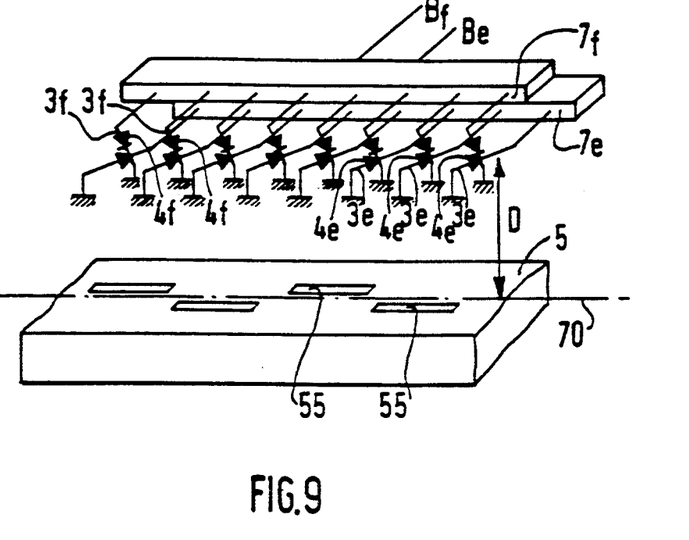

In FIG. 9 is shown a variant of the device of the invention, which makes possible the measurement of the diffracted field along two orthogonal polarizations. The antennae 3e of a first series are oriented at 45° with respect to the median axis 70, loaded by diodes 4e and connected to a multiplexer 7e receiving a low frequency signal Be, of frequency Fe. The antennae 3f of a second series are oriented perpendicularly to antennae 3e, loaded by diodes 4f and connected to a multiplexer 7f receiving a low frequency signal Bf, of frequency Ff. In a way not shown, the collected microwave signal, instead of undergoing a single synchronous low frequency detection, undergoes two synchronous detections, one at frequency Fe and the other at frequency Ff, which makes possible the simultaneous determination of the two components of the field at one point.

It would also be possible to use only a single multiplexer with twice the number of channels, by successively biassing each of the diodes 4e and 4f so as to determine successively the two components of the field at one point.

Figure 10:
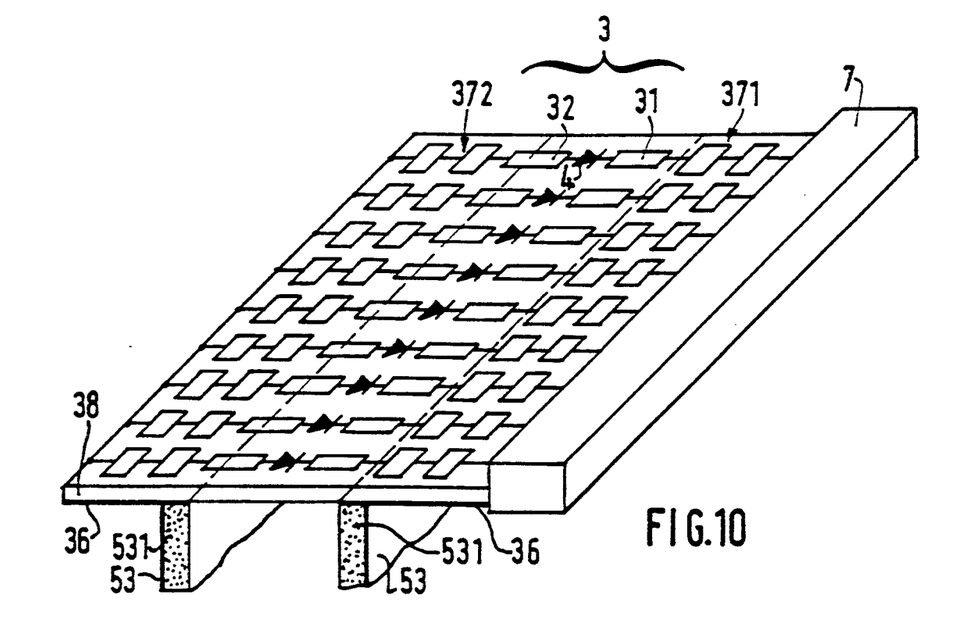
FIG. 10 shows in greater detail a variant of the arrangement of the doublet antennae of the device of FIG. 1.

In FIG. 10 has been shown in greater detail an arrangement of the doublet antennae 3 and their connection to multiplexer 7. A single dielectric plate 38 bears on the upper end of walls 53 covered with their absorbing layer 531. Two metal layers 36 are provided under plate 38, on each side of a zone in which the doublet antennae 3 are situated. On the upper face of plate 38, the two sections 31 and 32 of each doublet antenna 3 are formed by means of a conducting microstrip supported by plate 38.

The PIN diode 4 is connected to these two sections 31 and 32 which are each extended as a low pass filter 371 and 372 respectively, formed in a way known per se, above the metal layers 36, by varying the width of the microstrip so as to obtain alternation of narrow microstrip portions and wide microstrip portions. The low pass filters 371 are each connected to an output of multiplexer 7 and the low pass filters 372 are all connected to the electric ground. The low pass filters 371 and 372 behave like short circuits for the low frequency signal B and like open circuits for the signals at the microwave frequency.

In the preceding description, the case has always been considered in which the object has the microwave radiation passing therethrough, i.e. in the case where the diffracted microwave field is the transmitted field. This is not obligatory and it is also possible to measure, with the device of the invention, the field reflected by an object illuminated by microwave radiation or simultaneously the transmitted field and the reflected field, using if necessary several devices.

Similarly, in FIG. 1, a horn 2 has been shown for illuminating plank 1. This is not obligatory and it would be possible to use advantageously, instead of horn 2, a microwave radiation source comprising a guide structure having coupling antennae, identical to the one used for the collector but obviously without any doublet antenna. Such a guide structure is then placed at a few wavelengths from the object to be illuminated.

For some applications, it is advantageous to use a microwave radiation source with double biassing.

It is not obligatory to use PIN diodes and they may be replaced by photodiodes which can be biased by a laser beam or optical fibers.

Similarly, the guide structure such as guide 5, 5a, 5b and lines 5c and 5d are not necessarily terminated by a short circuit. Thus, they are often terminated by a matched load, as is known.

In the case where the object is not travelling, and when it is desired to have a two dimensional image of the object, it is obviously possible to juxtapose several devices in accordance with the above device.

The procedure for experimentally determining the distance D is the following, with reference to FIG. 1. With no object such as plank 1 interposed between horn 2 and the doublet antennae 3, these latter are illuminated uniformly. While circuit 8 controls successively the biassing of each of diodes 4 by means of signal B, as has been described, guide 5 is moved away from a position in which it is situated against the doublet antennae 3, while observing the displayed signal. At the beginning, oscillations are to be found corresponding to the periodicity of distribution of slots 55, but these oscillations are attenuated gradually as distance D increases. At the same time, the level of the received signal decreases. It is stopped when the field is uniform on the doublet antennae line, i.e. when the residual undulations are small enough to be compatible with the required precision. In general, this result is obtained for a distance D of the order of a few wavelengths. It will be noted that, by suitable calibration, the defects of the device can be corrected.

Naturally, the device may be used for testing the field radiated by industrial applicators and telecommunications or radar antennae, possibly provided with radomes.

What is claimed is:

1. An arrangement for point-by-point measuring a microwave radiation field diffracted by an object to be analyzed, comprising:
   (a) means for irradiating an elongated zone on the object with microwave radiation along a predetermined direction to generate the microwave radiation field to be measured;
   (b) a plurality of discrete, electric doublet antennae spaced apart of one another in a first plane along said predetermined direction, each doublet antenna having a center-loaded diode;
   (c) multiplexing means for successively biasing the diodes of the doublet antennae, each diode in its turn;
   (d) a single, elongated microwave guide extending between opposite guide ends along said predetermined direction;
   (e) a plurality of discrete, coupling antennae spaced apart of one another along said predetermined direction in a second plane generally parallel to, and spaced at a distance from, said first plane, to successively couple into the guide microwave radiations impinging on the coupling antennae during successive biasing of the diodes of the doublet antennae;
   (f) means for terminating one of the guide ends; and
   (g) means at the other of the guide ends for converting all the microwave radiations in the guide to a single output signal indicative of the microwave radiation field being measured.

2. The arrangement according to claim 1, wherein the irradiating means includes a microwave generator and a horn connected to the generator, said horn having a radiating aperture extending along the predetermined direction.

3. The arrangement according to claim 2; and further comprising a pair of walls extending along said predetermined direction between said first and second planes, and a layer of microwave radiation absorbent material on the walls.

4. The arrangement according to claim 3, wherein the walls are constituted of a metal material, and have metal flanges co-planar with said first plane.

5. The arrangement according to claim 1; and further comprising an impedance matching screen between said first plane and the object.

6. The arrangement according to claim 5, wherein the matching screen is a metal plane having openings disposed opposite each of the doublet antennae.

7. The arrangement according to claim 5, wherein the matching screen is a thick plate of dielectric material.

8. The arrangement according to claim 1, wherein the guide is a hollow, metal waveguide having walls, and wherein the coupling antennae are slots formed in one of the walls of the waveguide.

9. The arrangement according to claim 8, wherein the waveguide supports the propagation of an electromagnetic wave at a guide wavelength, and wherein the slots are spaced apart at one-half the guide wavelength.

10. The arrangement according to claim 8, wherein the guide has a median line extending along the predetermined direction, and wherein the slots extend parallel to, and laterally offset at a spacing from, the median line.

11. The arrangement according to claim 8, wherein the guide has a median line extending along the predetermined direction, and wherein the slots are located on, and inclined relative to, the median line.

12. The arrangement according to claim 1, wherein the guide is a microstrip line on a substrate, and wherein the coupling antennae are edges of conductive regions on the substrate.

13. The arrangement according to claim 1, wherein each doublet antenna includes two elongated sections extending along a common line at opposite ends of the respective center-loaded diode, and wherein the common line is generally perpendicular to said predetermined direction.

14. The arrangement according to claim 1, wherein each doublet antenna includes two elongated sections extending along a common line at opposite ends of the respective center-loaded diode, and wherein the common line is generally parallel to said predetermined direction.

15. The arrangement according to claim 13, wherein the coupling antennae are equivalent to magnetic doublets perpendicular to the common line.

16. The arrangement according to claim 1, wherein the multiplexing means includes a generator for generating a timing signal; and a multiplexer having an input for receiving the timing signal, and a plurality of outputs respectively connected to the doublet antennae.

17. The arrangement according to claim 16, wherein each doublet antenna includes two elongated conductive sections at opposite ends of the respective center-loaded diode, and further comprising a first plurality of low pass filters respectively connecting the outputs of the multiplexer to one of the sections of a respective doublet antenna, and a second plurality of low pass filters respectively connecting the other of the sections of a respective doublet antenna to ground.

18. The arrangement according to claim 17, wherein the sections of each doublet antenna, the low pass filter and the guide are all constituted of a single microstrip.

19. The arrangement according to claim 1, wherein the doublet antennae are arranged in two groups, each doublet antenna of one group extending generally orthogonally to a respective doublet antenna of the other group.

20. The arrangement according to claim 1, wherein the terminating means is a matched load.

21. The arrangement according to claim 1, wherein the terminating means is a short circuit.

* * * * *